United States Patent [19]
Wyrzykiewicz

[11] Patent Number: 5,629,150
[45] Date of Patent: May 13, 1997

[54] METHODS FOR CHARACTERIZING PHOSPHOROTHIOATE OLIGONUCLEOTIDES

[75] Inventor: Tadeusz K. Wyrzykiewicz, Carlsbad, Calif.

[73] Assignee: ISIS Pharmaceuticals, Inc., Carlsbad, Calif.

[21] Appl. No.: 113,993

[22] Filed: Aug. 30, 1993

[51] Int. Cl.$^6$ .......................... C07H 21/00; C07H 21/04
[52] U.S. Cl. ........................ 435/6; 536/25.3; 536/25.4; 435/91.1
[58] Field of Search .................... 536/25.34, 25.3, 536/25.4; 935/77; 435/6, 91.1

[56] References Cited

PUBLICATIONS

Agrawal, et al., Analytical study of phosphorothioate analogues of oligonucleotides using high-performance liquid chromatography, *J. Chrom.*, 1990, 509, 396–399.
Burgers, et al., Disastereomers of 5'-O-Adenosyl 3'-O-Uridyl Phosphorothioate: Chemical Synthesis and Enzymatic Properties, *Biochem.*, 1979, 18, 450–454.
Chuvpilo et al., "A Solid–Phase Method for DNA Sequencing," *Bioorg. Khim.*, 1980, 9, 163–1637.
Connolly, et al., Synthesis and Characterization of an Octanucleotide Containing the EcoRI Recognition Sequence with a Phosphorothioate Group at the Cleavage Site, *Biochem.*, 1984, 23(15), 3443–3453.
Connolly et al., "Stereospecific Substitution of Oxygen-18 for Sulfur in Nucleoside Phosphorothioates," *J. Biol. Chem.*, 1982, 257, 3382–3384.
Gait, "Purification and Sequence Analysis of Synthetic Oligodeoxyribonucleotides," *Oligonucleotide Synthesis a Practical Approach*, 1984, IRL Press, Chapter 6, pp. 135–151.
Greene & Wuts, *Protective Groups in Organic Synthesis*, (John Wiley & Sons, 1991), pp. 277–308.
Horn, et al., Solid supported hydrolysis of apurinic sites in synthetic oligonucleotides for rapid and efficient purification on reverse–phase cartridges, *Nucleic Acids Res.*, 1988, 16(4), 11559–11571.
Inoue, Synthesis and hybridization studies on two complementary nona (2'-O-methyl) ribonucleotides, et al., *Nucleic Acids Res.* 1987, 15, 6131.
Jagadeeswaran, et al., "Use of Reverse–Phase Chromatography in the Maxam–Gilbert Method of DNA Sequencing," *Gene Anal. Techn.*, 1986, 3, 79–85.
Jones, et al. Automating the Purification and Isolation of Synthetic DNA, *Biotechnology*, 1987, 5, 67–70.

Kawasaki, et al., Synthesis and Biophysical Stuides of 2'-dRIBO-2'-F Modified Oligonucleotides, *J. Med. Chem.*, in press 1993.
Koziolkiewicz et al., P–Chiral Analogues of Ogliodeoxyribonucleotides: Synthesis, Stereochemistry and Enzyme Studies, *Chemica Scripta*, 1986, 26, 251–260.
Lesnik, et al., "Oligodeoxynucleotides Containing 2'-O-Modified Adenosine: Synthesis and Effects on Stability of DNA:RNA Duplexes," *Biochemistry*, 32:7832–7838, 1993.
Lowe, et al., Synthesis of Adenosine 5'[(R)α–$^{17}$O] Triphosphate, *J.Chem.Soc.*, 1982, 595–598.
Maxam, et al., "Sequencing End–Labeled DNA with Base–Specific Chemical Cleavages," *Methods Enzymol.*, 1980, 65, 499–560.
Nielsen, et al., Synthesis and Characterization of Dinucleoside Phosphorodithioates, *Tetrahedron Lett.*, 1988, 29, 2911.
Porritt, et al., Use of the 2,4–Dinitrobenzyl Protecting Group in the Synthesis of Phosphorodithioate Analogues of Oligodeoxyribonucleotides, *Tetrahedron Letters*, 1990, 31(3), 1319–1322.
Iyer et al., 3H–1,2–Benzodithiole–3–one 1,1–Dioxide as an Improved Sulfurizing Reagent in the Solid–Phase Synthesis of Olgodeoxyribonucleoside Phosphorothioates, *J. Am. Chem. Soc.*, 1990, 112, 1253–1254.
Rosental, et al., Solid–phase methods for sequencing of nucleic acids I. Simultaneous sequencing of different oligodeoxyribonucleotides using a new, mechanically stable anion–exchange paper, *Nucleic Acids Res.*, 1985, 13, 1173–1184.
Sammons, et al., Synthesis of $R_p$ and $S_p$ [α wβO] ADP from $S_p$ and $R_p$ β–Cyanoethyl–Adenosine 5'–[1–Thiodiphosphate], *J. Biol. Chem.*, 1982, 257, 1138–1141.
Sonvenaupx, et al., The Organic Chemistry Underlying DNA Synthesis, *Bioorg. Chem.*, 1982, 14, 274–325.
Uhlmann, et al., Antisense Oligonucleotides: A New Therapeutic Principle, *Chem. Rev.*, 1990, 90, 4, 553–584.
Cook, P.D., Medicinal chemistry of antisense oligonucleotides—future opportunities, *Anti–Cancer Drug Design*, 1991, 6, 585–607.

*Primary Examiner*—Gary L. Kunz
*Attorney, Agent, or Firm*—Woodcock Washburn Kurtz Mackiewicz & Norris

[57] ABSTRACT

This invention presents novel methods for desulfurizing and sequencing phosphorothioate oligonucleotides. These methods allow easy access to the analysis of phosphorothioate oligonucleotides because these methods may be performed as a final step in oligonucleotide synthesis. The methods of the invention will permit rapid characterization of oligonucleotides and may be easily adapted to characterizing pharmaceutical formulations.

24 Claims, 11 Drawing Sheets

Cycle: 1

|    | STEP | FUNCTION NAME | NUM | TIME  | ACTIVE   | SAFE |
|----|------|---------------|-----|-------|----------|------|
|    | 1)   | Begin         | 106 |       |          | Yes  |
|    | 2)   | 18 to Waste   | 64  | 3.0   |          | Yes  |
|    | 3)   | 18 to Column  | 42  | 10.0  | AGCT5678 | Yes  |
|    | 4)   | Reverse Flush | 2   | 10.0  | AGCT5678 | Yes  |
|    | 5)   | Block Flush   | 1   | 4.0   | AGCT5678 | Yes  |
| 1  | 6)   | 10 TO COLUMN  | 200 | 20.0  | AGCT5678 | Yes  |
|    | 7)   | Wait          | 103 | 600.0 | AGCT5678 | Yes  |
| 2  | 8)   | 10 TO COLUMN  | 200 | 20.0  | AGCT5678 | Yes  |
|    | 9)   | Wait          | 103 | 600.0 | AGCT5678 | Yes  |
| 3  | 10)  | 10 TO COLUMN  | 200 | 20.0  | AGCT5678 | Yes  |
|    | 11)  | Wait          | 103 | 600.0 | AGCT5678 | Yes  |
| 4  | 12)  | 10 TO COLUMN  | 200 | 20.0  | AGCT5678 | Yes  |
|    | 13)  | Wait          | 103 | 600.0 | AGCT5678 | Yes  |
| 5  | 14)  | 10 TO COLUMN  | 200 | 20.0  | AGCT5678 | Yes  |
|    | 15)  | Wait          | 103 | 600.0 | AGCT5678 | Yes  |
| 6  | 16)  | 10 TO COLUMN  | 200 | 20.0  | AGCT5678 | Yes  |
|    | 17)  | Wait          | 103 | 600.0 | AGCT5678 | Yes  |
| 7  | 18)  | 10 TO COLUMN  | 200 | 20.0  | AGCT5678 | Yes  |
|    | 19)  | Wait          | 103 | 600.0 | AGCT5678 | Yes  |
| 8  | 20)  | 10 TO COLUMN  | 200 | 20.0  | AGCT5678 | Yes  |
|    | 21)  | Wait          | 103 | 600.0 | AGCT5678 | Yes  |
| 9  | 22)  | 10 TO COLUMN  | 200 | 20.0  | AGCT5678 | Yes  |
|    | 23)  | Wait          | 103 | 600.0 | AGCT5678 | Yes  |
| 10 | 24)  | 10 TO COLUMN  | 200 | 20.0  | AGCT5678 | Yes  |
|    | 25)  | Wait          | 103 | 600.0 | AGCT5678 | Yes  |
| 11 | 26)  | 10 TO COLUMN  | 200 | 20.0  | AGCT5678 | Yes  |
|    | 27)  | Wait          | 103 | 600.0 | AGCT5678 | Yes  |
|    | 28)  | Reverse Flush | 2   | 7.0   | AGCT5678 | Yes  |
|    | 29)  | Block Flush   | 1   | 4.0   | AGCT5678 | Yes  |
|    | 30)  | 18 to Column  | 42  | 10.0  | AGCT5678 | Yes  |
|    | 31)  | Reverse Flush | 2   | 7.0   | AGCT5678 | Yes  |

FIG.5a

|    |     |                |     |       |          |     |
|----|-----|----------------|-----|-------|----------|-----|
|    | 32) | Block Flush    | 1   | 4.0   | AGCT5678 | Yes |
|    | 33) | Cap Prep       | 103 | 3.0   | AGCT5678 | Yes |
|    | 34) | 18 to Waste    | 64  | 4.0   | AGCT5678 | Yes |
|    | 35) | Reverse Flush  | 2   | 7.0   | AGCT5678 | Yes |
|    | 36) | Block Flush    | 1   | 3.0   | AGCT5678 | Yes |
| 1  | 37) | Cap to Column  | 39  | 30.0  | AGCT5678 | Yes |
|    | 38) | Wait           | 103 | 600.0 | AGCT5678 | Yes |
| 2  | 39) | Cap to Column  | 39  | 30.0  | AGCT5678 | Yes |
|    | 40) | Wait           | 103 | 600.0 | AGCT5678 | Yes |
| 3  | 41) | Cap to Column  | 39  | 30.0  | AGCT5678 | Yes |
|    | 42) | Wait           | 103 | 600.0 | AGCT5678 | Yes |
| 4  | 43) | Cap to Column  | 39  | 30.0  | AGCT5678 | Yes |
|    | 44) | Wait           | 103 | 600.0 | AGCT5678 | Yes |
| 5  | 45) | Cap to Column  | 39  | 30.0  | AGCT5678 | Yes |
|    | 46) | Wait           | 103 | 600.0 | AGCT5678 | Yes |
| 6  | 47) | Cap to Column  | 39  | 30.0  | AGCT5678 | Yes |
|    | 48) | Wait           | 103 | 600.0 | AGCT5678 | Yes |
| 7  | 49) | Cap to Column  | 39  | 30.0  | AGCT5678 | Yes |
|    | 50) | Wait           | 103 | 600.0 | AGCT5678 | Yes |
| 8  | 51) | Cap to Column  | 39  | 30.0  | AGCT5678 | Yes |
|    | 52) | Wait           | 103 | 600.0 | AGCT5678 | Yes |
| 9  | 53) | Cap to Column  | 39  | 30.0  | AGCT5678 | Yes |
|    | 54) | Wait           | 103 | 600.0 | AGCT5678 | Yes |
| 10 | 55) | Cap to Column  | 39  | 30.0  | AGCT5678 | Yes |
|    | 56) | Wait           | 103 | 600.0 | AGCT5678 | Yes |
| 11 | 57) | Cap to Column  | 39  | 30.0  | AGCT5678 | Yes |
|    | 58) | Wait           | 103 | 600.0 | AGCT5678 | Yes |
| 12 | 59) | Cap to Column  | 39  | 30.0  | AGCT5678 | Yes |
|    | 60) | Wait           | 103 | 600.0 | AGCT5678 | Yes |
| 13 | 61) | Cap to Column  | 39  | 30.0  | AGCT5678 | Yes |
|    | 62) | Wait           | 103 | 600.0 | AGCT5678 | Yes |
|    | 63) | 18 to Waste    | 64  | 4.0   | AGCT5678 | Yes |
|    | 64) | Reverse Flush  | 2   | 7.0   | AGCT5678 | Yes |

FIG.5b

| 65) | Block Flush | 1 | 3.0 | AGCT5678 | Yes |
| 66) | 18 to Column | 42 | 10.0 | AGCT5678 | Yes |
| 67) | Flush to Waste | 4 | 6.0 | AGCT5678 | Yes |
| 68) | 18 to Column | 42 | 10.0 | AGCT5678 | Yes |
| 69) | Reverse Flush | 2 | 7.0 | AGCT5678 | Yes |
| 70) | Block Flush | 1 | 3.0 | AGCT5678 | Yes |
| 71) | End | 107 | | | Yes |

Cycle used for automatic desulfurization (ABI 394B).
bottle 10 - solution of t-butylamine/pyridine (1:9, v/v)
bottle 11 - solution A 0.48M solution of $I_2$ in THF/$H_2O$
bottle 12 - solution of N-Methylimidazole in THF/$H_2O$

METHODS FOR CHARACTERIZING PHOSPHOROTHIOATE OLIGONUCLEOTIDES

FIELD OF THE INVENTION

This invention relates to the field of oligonucleotides. In particular this invention relates to methods for desulfurizing and sequencing phosphorothioate oligonucleotides.

BACKGROUND

It is well known that most of the bodily states in mammals including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another.

Prior attempts at antisense therapy have provided oligonucleotides or oligonucleotide analogs that are designed to bind in a specific fashion to—which are specifically hybridizable with—a specific mRNA by hybridization. Such oligonucleotides and oligonucleotide analogs are intended to inhibit the activity of the selected mRNA—to interfere with translation reactions by which proteins coded by the mRNA are produced—by any of a number of mechanisms. The inhibition of the formation of the specific proteins that are coded for by the mRNA sequences interfered with have been hoped to lead to therapeutic benefits; however there are still problems to be solved. See generally, Cook, P. D. *Anti-Cancer Drug Design* 1991, 6,585; Cook, P. D. *Medicinal Chemistry Strategies for Antisense Research, in Antisense Research & Applications*, Crooke, et al., CRC Press, Inc.; Boca Raton, Fla., 1993; Uhlmann, et al., A. *Chem. Rev.* 1990, 90, 543.

Oligonucleotides and oligonucleotide analogs are now accepted as therapeutic agents holding great promise for therapeutics and diagnostics methods. But applications of oligonucleotides and oligonucleotide analogs as antisense agents for therapeutic purposes, diagnostic purposes, and research reagents often require that the oligonucleotides or oligonucleotide analogs be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides and oligonucleotide analogs toward nuclease degradation.

A serious deficiency of unmodified oligonucleotides for these purposes, particularly antisense therapeutics, is the enzymatic degradation of the administered oligonucleotides by a variety of intracellular and extracellular ubiquitous nucleolytic enzymes.

A number of chemical modifications have been introduced into antisense agents—oligonucleotides and oligonucleotide analogs—to increase their therapeutic activity. Such modifications are designed to increase cell penetration of the antisense agents, to stabilize the antisense agents from nucleases and other enzymes that degrade or interfere with their structure or activity in the body, to enhance the antisense agents' binding to targeted RNA, to provide a mode of disruption (terminating event) once the antisense agents are sequence-specifically bound to targeted RNA, and to improve the antisense agents' pharmacokinetic and pharmacodynamic properties. It is unlikely that unmodified, "wild type," oligonucleotides will be useful therapeutic agents because they are rapidly degraded by nucleases.

Phosphorothioate modified oligonucleotides are capable of terminating RNA by activation of RNase H upon hybridization to RNA although hybridization arrest of RNA function may play some part in their activity. Phosphoramidites have been disclosed as set forth in U.S. patent application assigned to a common assignee hereof, entitled "Improved Process for Preparation of 2'-O-Alkylguanosines and Related Compounds," Ser. No. 918,362, the disclosures of which are incorporated herein by reference to disclose more fully such modifications. However, all reported modifications of the sugar-phosphate backbone, with the exception of phosphorothioates and phosphorodithioates, obliterate the RNase H terminating event. Cook, 1991, supra; Cook, 1993, supra; Uhlmann, et al., A. *Chem. Rev.* 1990, 90, 543. Heteroduplexes formed between RNA and oligodeoxynucleotides bearing 2'-sugar modifications, RNA mimics such as fluoro and alkoxys, do not support RNase H-mediated cleavage. These modified heteroduplexes assume an A form helical geometry as does RNA-RNA heteroduplexes which also do not support RNase H cleavage; Kawasaki, et al., *J. Med. Chem.*, in press 1993; Lesnik, et al., *Biochemistry*, submitted 1993; Inoue, et al., *Nucleic Acids Res.* 1987, 15, 6131.

Oligonucleotides having phosphodiester linkages replaced by phosphorothioate residues have been demonstrated to be a sequence specific regulators of gene expression in eucaryotic and procaryotic systems. Chemical stability of these compounds in combination with efficient automatic synthesis, Iyer, et al., *J. Am. Chem. Soc.*, 1990, 112, 1253–1254, results in the oligonucleotide phosphorothioates being the best to date candidates for practical application as "antisense" therapeutic agents. Eckstein, *Oligonucleotide and Analogs, A Practical Approach*, 1991, IRL Press, pp. 87–103.

Potential applications of phosphorothioate oligonucleotides as drugs have created a new challenge related to large-scale synthesis, purification, and analysis of the products. Although improvements in automatic assembling of phosphorothioate DNA analogs allows efficient synthesis of oligonucleotides, yet there are always occasional failures due to chemical and mechanical problems. Due to these problems, it is important to routinely confirm the sequence of these oligonucleotide products by direct sequence analysis. Replacing the non-bridging oxygen in the backbone with sulfur leads to desirable bio-chemical characteristics, including: resistance towards nucleases, retention of the ability to form double helix, solubility in water, chirality at phosphorus and stability to base catalyzed hydrolysis. Uhlmann, supra, 553–584. Unfortunately these features, advantageous in therapeutic technology, are disadvantageous from an analytical point of view, particularly problematic, is the chirality of the phosphorous atom.

In contrast to natural DNA, the phosphorus center of phosphorothioate oligonucleotides is chiral. Because of the stereospecificity of the coupling chemistry for oligonucleotide with many phosphorothioate linkages (n), there can be $2^n$ possible diastereomers. Stereospecificity of nucleases for one or the other diastereoisomers of the phosphorothioate linkages varies. For instance S isomers are cleaved by nucleases P1 or S1, while R isomers can be cleaved by snake venom phosphodiesterase. Uhlmann, et al., Chem. Rev., 1990, 90, 4, 553–584. For the above reasons, direct cleavage of the oligonucleotide phosphorothioates with enzymes may lead to incomplete degradation, with yield influenced by variable, sequence specific populations of different stereoisomers. Described problems can be overcome by conversion of the oligonucleotide phosphorothioates into their phosphodiester analogs.

Several workers have studied replacing the sulfur atoms of the phosphorothioate oligonucleotides to attain the phosphodiesters. For example, it has been demonstrated that the sulfur in phosphorothioates can be replaced by oxygen when oxidation is carried out with iodine in pyridine in solution (phosphorothioate triesters are inert under these conditions). Connoly, et al., Biochem., 1984, 23(15), 3443–3453. There are also other methods available for desulfurization of phosphorothioates using 2-iodoethanol, Gish, Science, 1988, 240, 1520–1522; sodium metaperiodate, Agarval, et al., J. Chrom., 1990, 509, 396–399; iodine-bicarbonate, Burgers, et al., Biochem., 1979, 18, 450–454; cyanogen bromide, Sammons, et al., J. Biol. Chem., 1982, 257, 1138–1141; bromine, Lowe, et al., J. Chem. Soc., 1982, 595–598; and N-bromosuccinimide, Conoly, et al., J. Biol. Chem., 1982, 257, 3382–3384. Desulfurization of a phosphorodithioate dimer TpT was done using a solution of iodine in tetrhyrdofuran/water/n-methylimidazole. Porritt, et al., Tetrahedron Letters, 1990, 31(3), 1319–1322.

However, these methods were directed to oligonucleotides containing only one or two phosphorothioates; these methods are impractical because pharmaceutical formulations will typically contain many more nucleotide units. Desulfurized oligonucleotides have been typically analyzed using high performance liquid chromatography (HPLC) or enzymatic digestion; these methods are also impractical.

Oligonucleotides are typically characterized by sequencing to verify their composition. Generally, sequencing of short oligonucleotide phosphodiesters (10–25 size range) can be determined by partial enzymatic digestion ("wandering spot" method), Gait, Oligonucleotide Synthesis a Practical Approach, 1984, IRL Press, pp. 135–151, or by chemical sequencing, Maxam, et al., Gene, 1980, 10, 177. Chemical sequencing of oligonucleotides is based on the chemical modifications of the heterocyclic bases followed by cleavage of the oligonucleotide chain at the "modification" site under basic conditions.

Another limitation of the above described sequencing procedures, is that these procedures were designed to work in solution and need to be followed by time consuming and scale-limiting purification steps. This is also highly impractical.

DNA fragments have been sequenced on the ion-exchange cellulose-based carriers, Chuvpilo, et al., Bioorg. Khim., 1980, 9, 1694–1697, and $C_{18}$ reverse-phase column, Jagadeeswaran, et al., Gene Anal. Tech., 1986, 3, 79–85. However, few attempts have been made to carry out sequencing on a solid support to eliminate losses and accelerate the process of sequence analysis.

Thus, there still remains a need for methods of characterizing oligonucleotides that are rapid, efficient, and readily adaptable to current pharmaceutical applications. The present invention addresses these, as well as other needs.

SUMMARY OF THE INVENTION

The present invention discloses solid supported desulfurization methods allowing easy access to sequence analysis of oligonucleotide phosphorothioates. It has been discovered that oligonucleotide phosphorothioates can be desulfurized on a solid support (i.e., controlled-pore glass (CPG), equipped with standard ester linkage) using iodine solutions, such as iodine in THF/water/N-methylimidazole.

Desulfurization on the solid support can be used as a step before sequencing, leading to a rapid method of sequence analysis of the oligonucleotide phosphorothioates. Application of the solid supported reactions in both the desulfurization and sequencing steps allows separation of products from the reaction mixtures by simple washing steps, opening the way to fully automated analysis. Additionally, the solid support desulfurization can be used as a first step in base ratio analysis, such that the second step may be standard digestion and analysis.

The disclosed desulfurization is preferably performed as a last step of oligonucleotide synthesis. It is preferably practiced during solid phase support synthesis of the oligonucleotide synthesis while the oligonucleotide is still on the solid phase support. It includes two steps. The first step selectively removes protecting groups used in the synthesis from the oligonucleotoide precursor without affecting the linkage used to hold the growing oligonucleotide on the solid phase support. Typically a succinate ester is used as the linkage in the solid phase oligonucleotide synthesis to attach the oligonucleotide to the solid phase support. The oligonucleotide protecting groups include cyanoethyl groups used to protect phosphorothioate moieties of the oligonucleotides. For discussion of protective groups in organic synthesis see Greene & Wuts, Protection Groups in Organic Synthesis, (John Wiley & Sons, 1991). In the second step, the support-bound oligonucleotide phosphorothioate is treated with a solution of iodine in THF/water/N-methylimidazole, which converts the phosphorothioate to its phosphodiester analog. This renders the oligonucleotide amenable to sequencing.

The invention also presents an automated desulfurization procedure that can be performed with application of standard DNA synthesizers, and successfully combined with solid supported chemical sequencing methods. This automation permits rapid, simultaneous analysis of many oligonucleotide and oligonucleotide analogs.

The disclosed procedure also has potential to handle unlimited amounts of samples. It is also possible to label oligonucleotides or oligonucleotide analogs on the solid support with fluorescent or other markers that are unique for different base modifications, and run obtained DNA fragments in the same lane on an electrophoretic gel. Serial identification of the labels specific for each base would provide sequence for each of the analyzed fragments.

DETAILED DESCRIPTION OF PREFERRED EMBODIMENTS

The invention presents rapid methods for the sequence analysis of oligonucleotide phosphorothioates comprising desulfurization and sequencing of oligonucleotides on the solid support. Desulfurization on the solid support is performed at the end of synthesis of an oligonucleotide product. Application of the solid supported reactions, in both steps of the procedure—desulfurization and sequencing, allows the products from the reaction mixtures to be separated by simple washing steps, opening way to fully automated analysis.

In the context of this invention, a "nucleoside" is a nitrogenous heterocyclic base linked to a pentose sugar, either a ribose, deoxyribose, or derivatives or analogs thereof. The term "nucleotide" means a phosphoric acid ester of a nucleoside comprising a nitrogenous heterocyclic base, a pentose sugar, and one or more phosphate or other backbone forming groups; it is the monomeric unit of an oligonucleotide. The term "oligonucleotide" refers to a plurality of joined nucleotide units formed in a specific sequence from naturally occurring heterocyclic bases and pentofuranosyl equivalent groups joined through phosphodiester or other backbone forming groups. Nucleotide units may include the common bases such as guanine, adenine, cytosine, thymine, or derivatives thereof. The pentose sugar may be deoxyribose, ribose, or groups that substitute therefore. The terms "antisense agents" as used in the context of this invention encompass oligonucleotides and oligonucleotide analogs. In the context of this invention, phosphate derivatives include phosphorothioates, methyl phosphonates, phosphoramidites, phosphotriesters, and any other groups known to those skilled in the art. In the context of this invention, "oligonucleotide product" means the protected oligonucleotide bound to the solid support or a protected oligonucleotide.

"Sugar moiety" as used in the context of this invention refers to naturally occurring sugars, such as ribose or deoxyribose, and sugars and non-sugar analogs that have been functionalized to change certain properties.

"Oligonucleotide analogs" or "modified oligonucleotides" as used in connection with this invention, refer to compositions that function similarly to natural oligonucleotides but that have non-naturally occurring portions. Oligonucleotide analogs or modified oligonucleotides may have altered sugar moieties, altered bases, both altered sugars and bases, or altered inter-sugar linkages, for example phosphorothioates and other sulfur containing species which are known for use in the art.

In the context of the invention, "improved pharmacodynamic property" means improved antisense agent uptake, enhanced antisense agent resistance to degradation, and/or strengthened sequence-specific hybridization with RNA. "Improved pharmacokinetic property" means improved oligonucleotide uptake, distribution, metabolism or excretion.

In one aspect of the invention, manual methods for analyzing and characterizing phosphorothioate oligonuceltoides bound to a solid support are provided. In certain preferred embodiments, the method comprises removing the protecting groups, such as cyanoethyl groups, preferably using a solution of tert-butylamine in pyridine; and treating the deprotected oligonucleotide with an iodine solution comprising at least about 10 equivalents of iodine per sulfur atom of the oligonucleotide, preferably at least about 15 equivalents, more preferably at least about 20 equivalents.

In other preferred embodiments, the iodine solution comprises iodine dissolved in pyridine and water, preferably the pyridine and water are in an approximate volume ratio of 1:1. In still other preferred embodiments, the iodine is in solution in an ethanol sodium bicarbonate buffer. More preferably, the iodine is in a solution comprising tetrahydrofuran, water, and N-methylimidazole. In certain preferred embodiments, the tetrahydrofuran, water, and N-methylimidazole are present in a volume ratio of about 16/6/1.

In certain preferred embodiments, the oligonucleotide comprises from 10 to about 50 nucleotide units. Preferably, the desulfurization is continued for a time sufficient to remove at least about 98% of the sulfur from the oligonucleotide.

Desulfurization of the oligonucleotide phosphorothioates requires that phosphate protecting groups be removed before desulfurization. Deprotection is necessary because only phosphorothioates can be easily converted to their phosphodiester analogs. The strategy, in the present oligonucleotide synthesis, employs a combination of the base-labile permanent protecting groups for phosphate (2-cyanoethyl) and aglycone residues (N-acyl) in combination with succinate linkage, placed between solid support and oligonucleotide, clearable also under basic condition. Sonvenaux, et al., *Bioorg. Chem.*, 1982, 14, 274–325. The 2-cyanoethyl phosphate protecting groups are cleaved by treating the oligonucleotide phosphorothioate bounded to the CPG with solutions such as t-butylamine in pyridine, for a time effective to remove protecting groups. The treatment time is preferably between about 1 to 2 hours, more preferably about 1.5 hours. Horn, et al., *Nucleic Acids Res.*, 1988, 16(4), 11559–11571. Thus, in order to leave oligonucleotides on the solid support, deprotection of the phosphoroester residues needs to be done selectively without hydrolysis of the linkage.

Other methods of deprotecting the phosphate groups will be readily apparent to those skilled in the art and may be used without detracting from the spirit of the invention.

Deprotecting solution is removed by washing, and the obtained oligonucleotide phosphodiesters are subjected to desulfurization. The solid supported desulfurization reaction was performed using THF/water/N-methylimidazole and iodine dissolved in mixture of pyridine and water, preferably in a 1/1, v/v ratio, or iodine-bicarbonate. The best result was obtained for desulfurization with iodine in mixture of tetrahydrofuran/water/N-methylimidazole.

In a more preferred embodiment, the deprotection of the phosphates and desulfurization are carried out using an automated procedure and can be performed with application of standard DNA synthesizers. These methods comprise delivering an iodine solution to the solid support, thereby desulfurizing the oligonucleotide product. The iodine solution is prepared by premixing first and second independent solutions during delivery to the solid support, wherein the first solution comprises iodine and tetrahydrofuran/water, and the second solution comprises tetrahydrofuran/water/N-methylimidazole. In certain preferred embodiments, the first solution comprises tetrahydrofuran and water in a volume ratio of about 10–16/1–6, preferably the ratio is almost 12–16/3–6, more preferably the ratio is about 16/6 and the second solution comprises tetrahydrofuran, water, and N-methylimidazole in a volume ratio of about 10–16/1–6/1–5, preferably the ratio is 12–16/3–6/3–5, more preferably the ratio is about 16/6/1, preferably the concentration of iodine in solution A is between about 0.40M to 0.55M, preferably about 0.45M, more preferably 0.48M.

Figure 1:
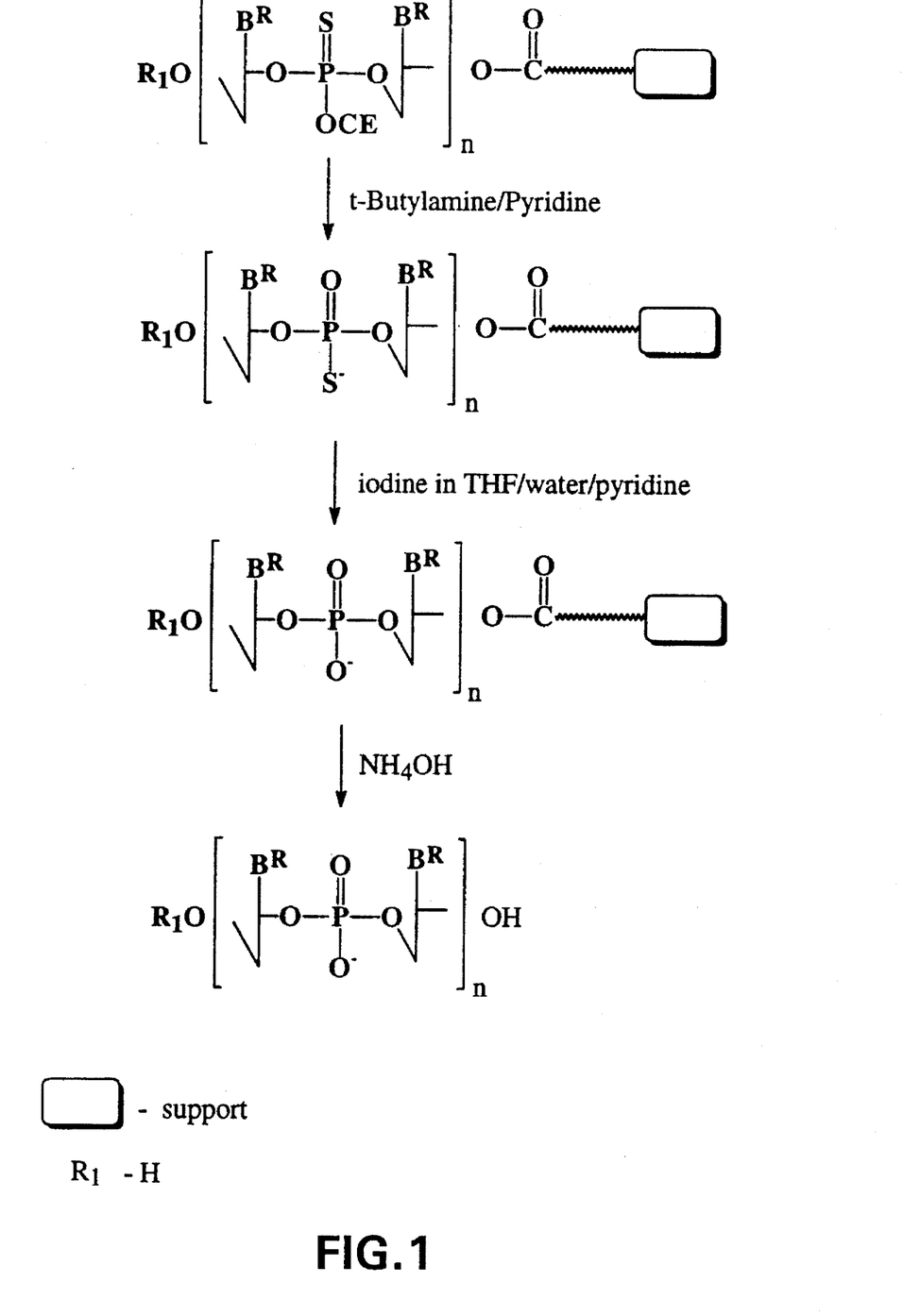
FIG. 1 is flow scheme of a first process for desulfurizing oligonucleotides on a solid support.
Figure 2:
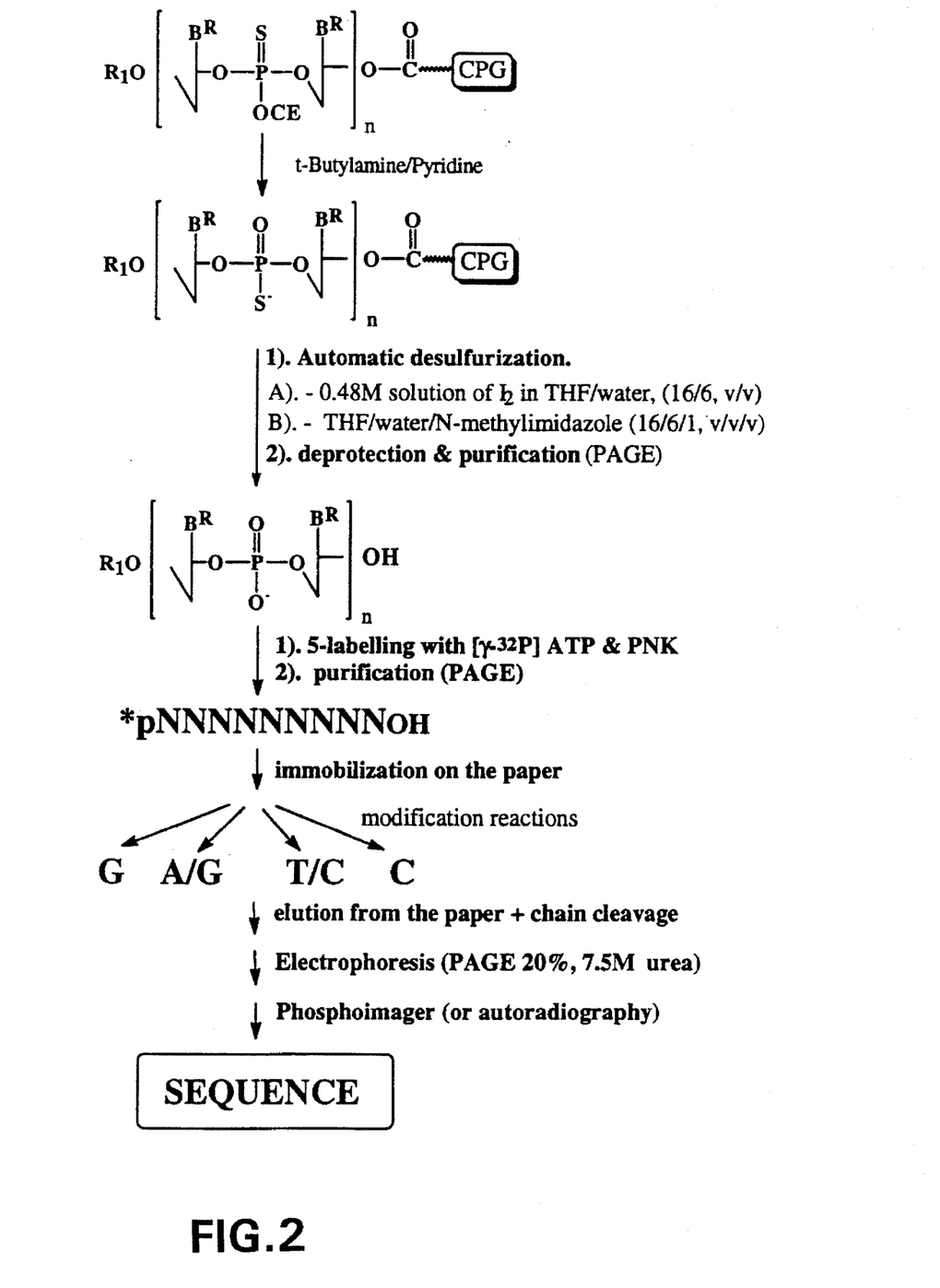
FIG. 2 is a flow scheme of an automated second process for desulfurizing and sequencing oligonucleotides bound to a solid support.

In a further preferred embodiment, the method further comprises labeling the desulfurized oligonucleotide product; purifying the labeled oligonucleotide product; immobilizing the purified oligonucleotide product on an ion-exchange carrier; modifying the base units of the oligonucleotide product, thereby generating oligonucleotide fragments forming lanes of guanine, adenine and guanine, thymine and cytosine; fractioning the oligonucleotide fragments; and imaging the oligonucleotide fragments. The sequence analysis is depicted in FIG. 2.

A commercially available support developed by Rosental, et al., *Nucleic Acids Res.*, 1985, 13, 1173–1184, is used due to its chemical stability, mechanical resistance, and relatively high loading capacity (up to 200 µg of DNA per cm$^2$). However, other solid supports may be used without departing from the spirit of the invention.

Generally, the sequencing step may be carried out by labeling the desulfurized oligonucleotide on the solid support with [$\gamma$-$^{32}$P] ATP, and then purifying the oligonucleotide using polyacrylamide gel electrophoresis (PAGE). The oligonucleotide is then immobilized on an ion-exchange carrier. Sequencing may proceed by chemically modifying the bases under the following conditions: for the cytosine lane, hydroxylamine hydrochloride having a pH between about 4–5, preferably about 5–6, more preferably 6; for the adenine/guanine lane, formic acid solution of concentrations of about 80–100%, preferably about 90–100%, more preferably about 88%; and for the guanine lane, dimethyl sulfate in ammonium formate buffer having a pH between 3–5, preferably about 3–4, more preferably 3.5. Modification of the thymine/cytosine lane was obtained by treating with potassium permanganate. Oligonucleotide fragments generated by sequencing procedure were fractionated by PAGE and visualized using a phosphorimager. Phosphorimager analysis was performed using instrument from Molecular Dynamics.

Other methods of purifying the oligonucleotides known to those skilled in the art may be used without departing from the spirit of the invention, such as HPLC or digestion. Any methods known to those skilled in the art may be used for labeling the oligonucleotides or modifying the bases and are fully contemplated by the invention.

Simultaneous sequencing of the desulfurized oligonucleotides and their phosphodiester analogues always generated similar cleavage patterns. The obtained cleavage patterns were clear and allowed to read the sequence. Interestingly enough cleavage patterns of desulfurized oligomers were more selective, compared to their diester analogues.

It is known that in the case of chemical sequencing one may expect certain ambiguities occurring in sequence determination. However, sequencing of oligonucleotides desulfurized on the solid support gave clear cleavage patterns allowing sequence confirmation of the analyzed oligomers using only four standard cleavage reactions.

One may assume that mechanism of sulfur displacement with oxygen (using iodine in mixture of THF/water/N-methylimidazole) should be similar for oligonucleotide phosphorodithioates, Nielsen, et al., *Tetrahedron Lett.*, 1988, 29, 2911, and phosphoroselenoates, Koziolkiewicz, et al., *Chemica Scripta*, 1986, 26, 251–260. Due to that, the above methods could possibly be used for sequencing of phosphorodithioates and phosphoroselenoates.

The invention is further described in the following examples. These examples should not be construed as limiting the appended claims.

EXAMPLES

EXAMPLE 1

Synthesis of Oligonucleotide Phosphorothioates

Oligonucleotide phosphorothioates of the sequences TTG CTT CCA TCT TCC TCG TC and GCG TTT GCT CTT CTT CTT GCG, used in described studies were synthesized in 250 µmole scale on CPG, using 8800 Millipore DNA synthesizer and standard phosphoroamidite chemistry. Jones, et al., *Biotechnology*, 1987, 5, 67–70. 3H-1,2-Benzodithiol-3-one 1,1-dioxide was used as a sulfurizing agent. Iyer, supra. 4,4-Dimethoxytritylprotecting group was removed on the solid support before desulfurization.

EXAMPLE 2

Desulfurization on the solid support

A. Manual desulfurization

1) Removal of the 2-cyanoethyl phosphate protecting groups.

After completing the synthesis, 5'-O-DMT protecting groups were removed and support containing oligonucleotide (20 mg of CPG) was washed with $CH_3CN$, $CH_2Cl_2$ (10 ml each) and dried in a stream of argon. Then oligomers on the support were treated with mixture of t-butyl amine and pyridine (1/9, v/v) at room temperature for 90 minutes. Then the support was transferred on funnel and washed with $CH_3CN$, $CH_2Cl_2$ (10 ml each) and air dried.

2) Removal of the sulfur.

After completion of the above step, the CPG bearing oligonucleotide phosphorothioates were treated for 120 minutes with a solution of iodine in $THF/H_2O/N$-Methylimidazole (16/6/1, v/v/v) (20 eq. of iodine per each atom of sulfur). Then the support was transferred on funnel and washed with $CH_3CN$, $CH_2Cl_2$, and air dried.

B. Automatic desulfurization

Figure 5A:
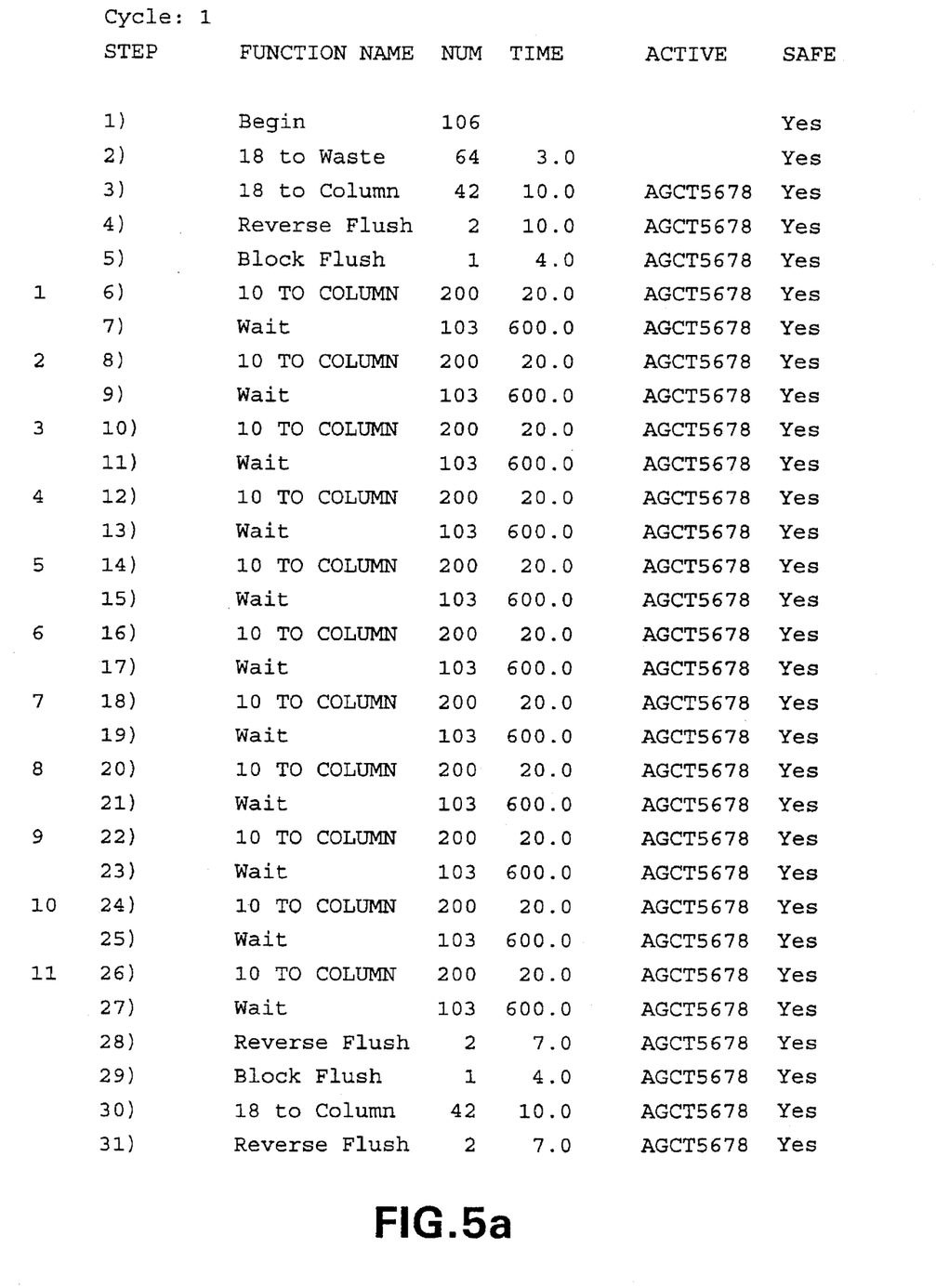
FIGS. 5A, 5B and 5C illustrate the cycle for a DNA synthesizer for performing a process of the invention.
Figure 5B:
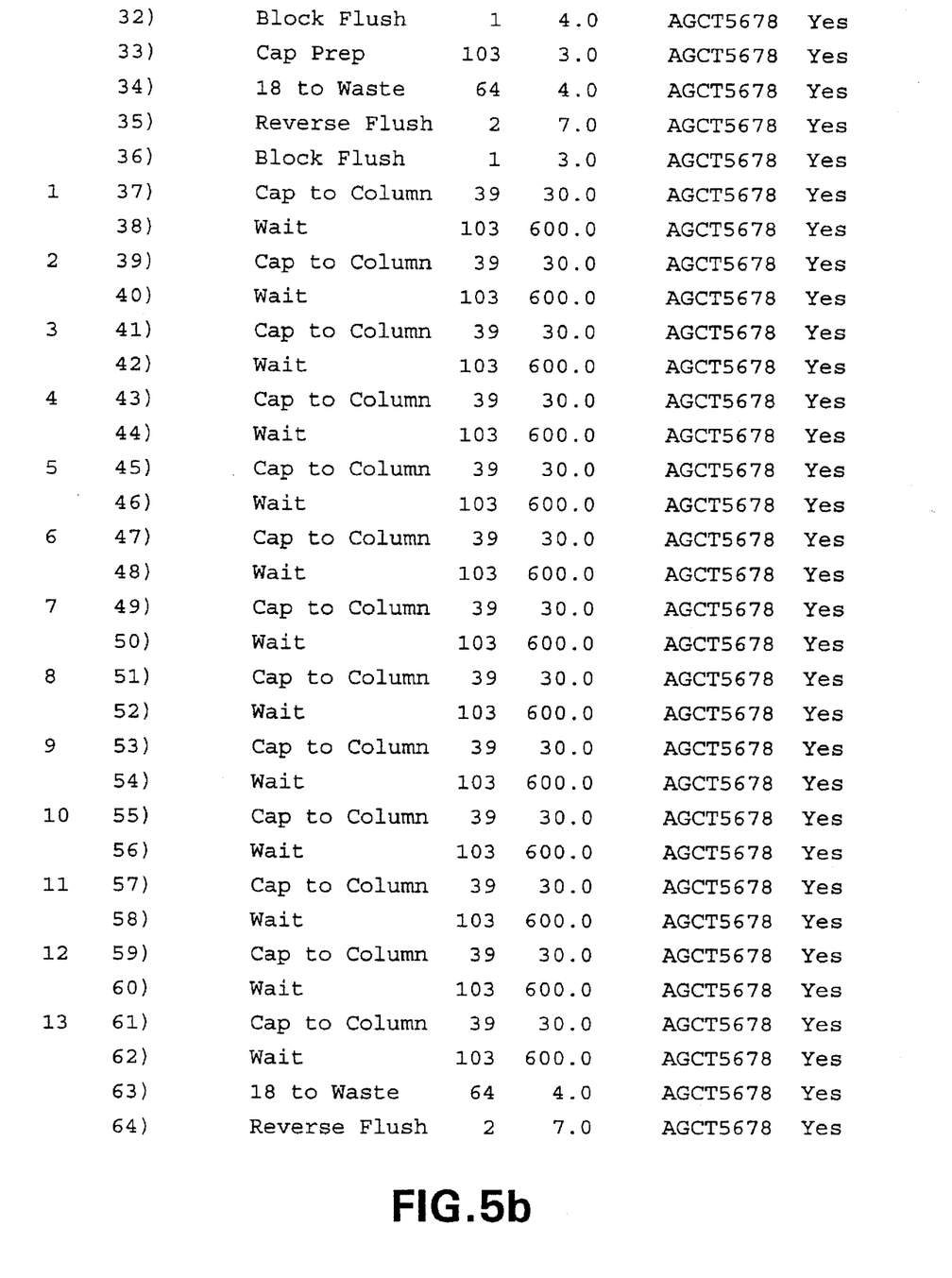
Figure 5C:
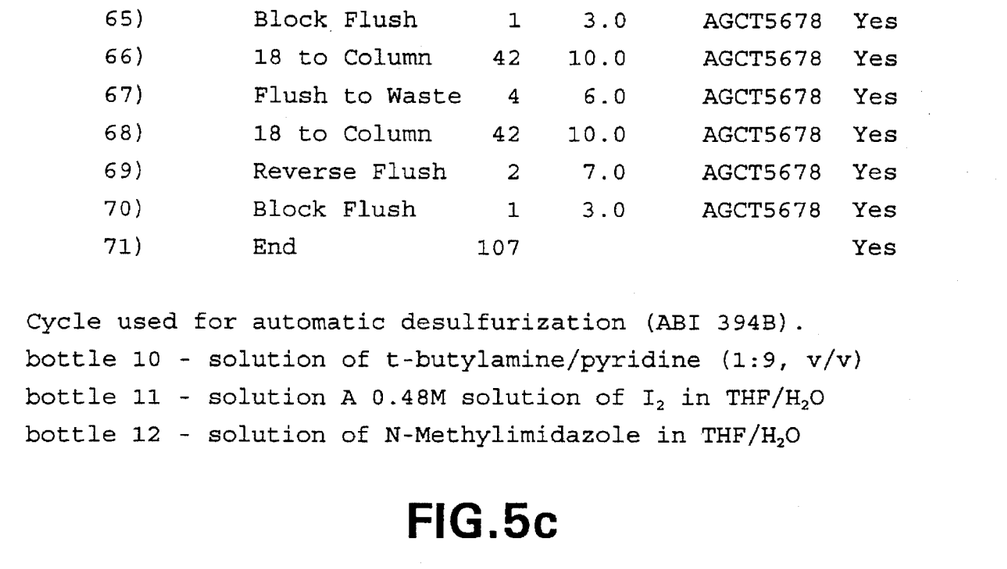
Figure 6A:
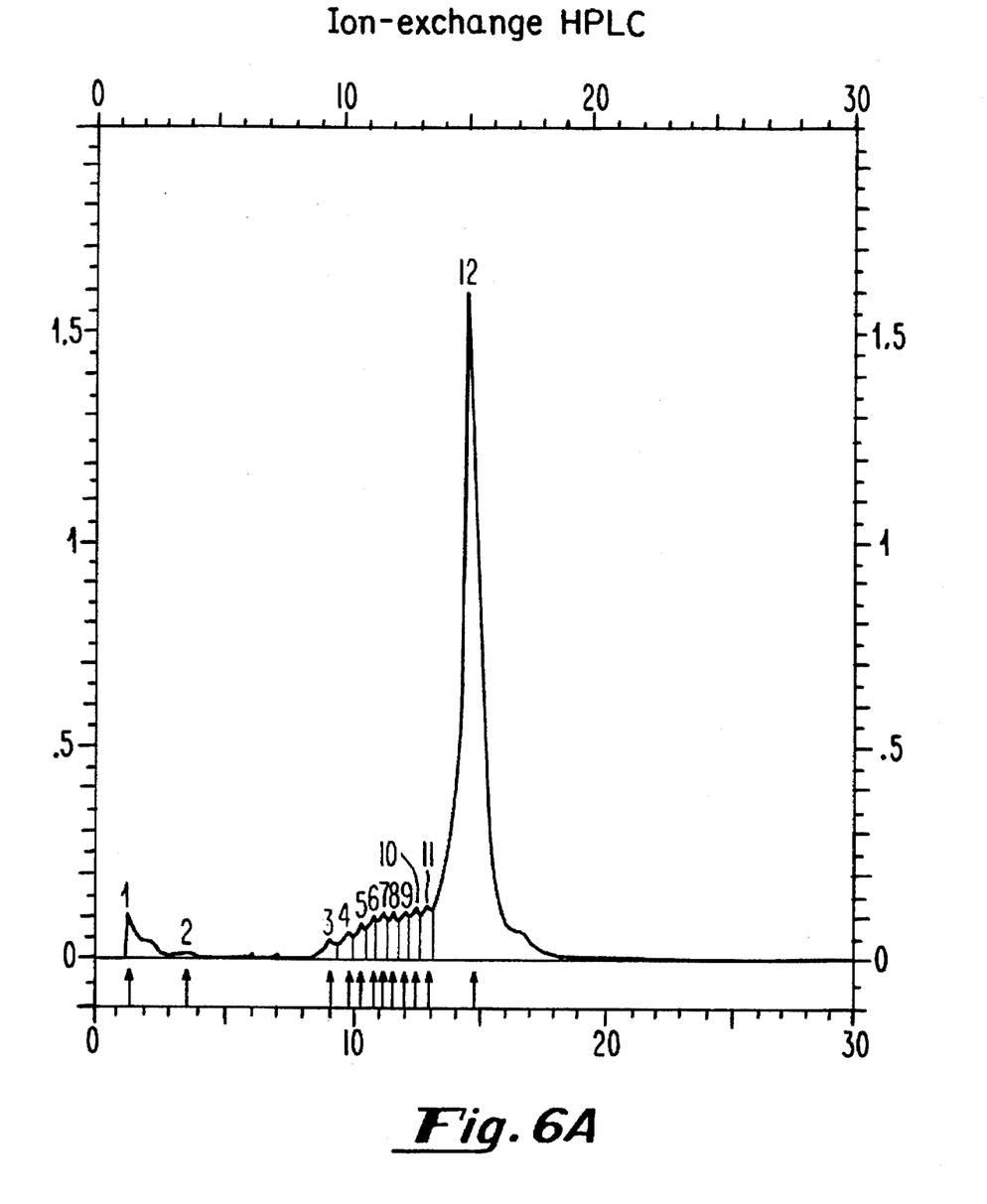
FIG. 6A is a representation of an ionic exchange HPLC trace for a desulfurized oligonucleotide phosphorothioate of the same sequence as is represented in FIG. 4, illustrating starting material.
Figure 6B:
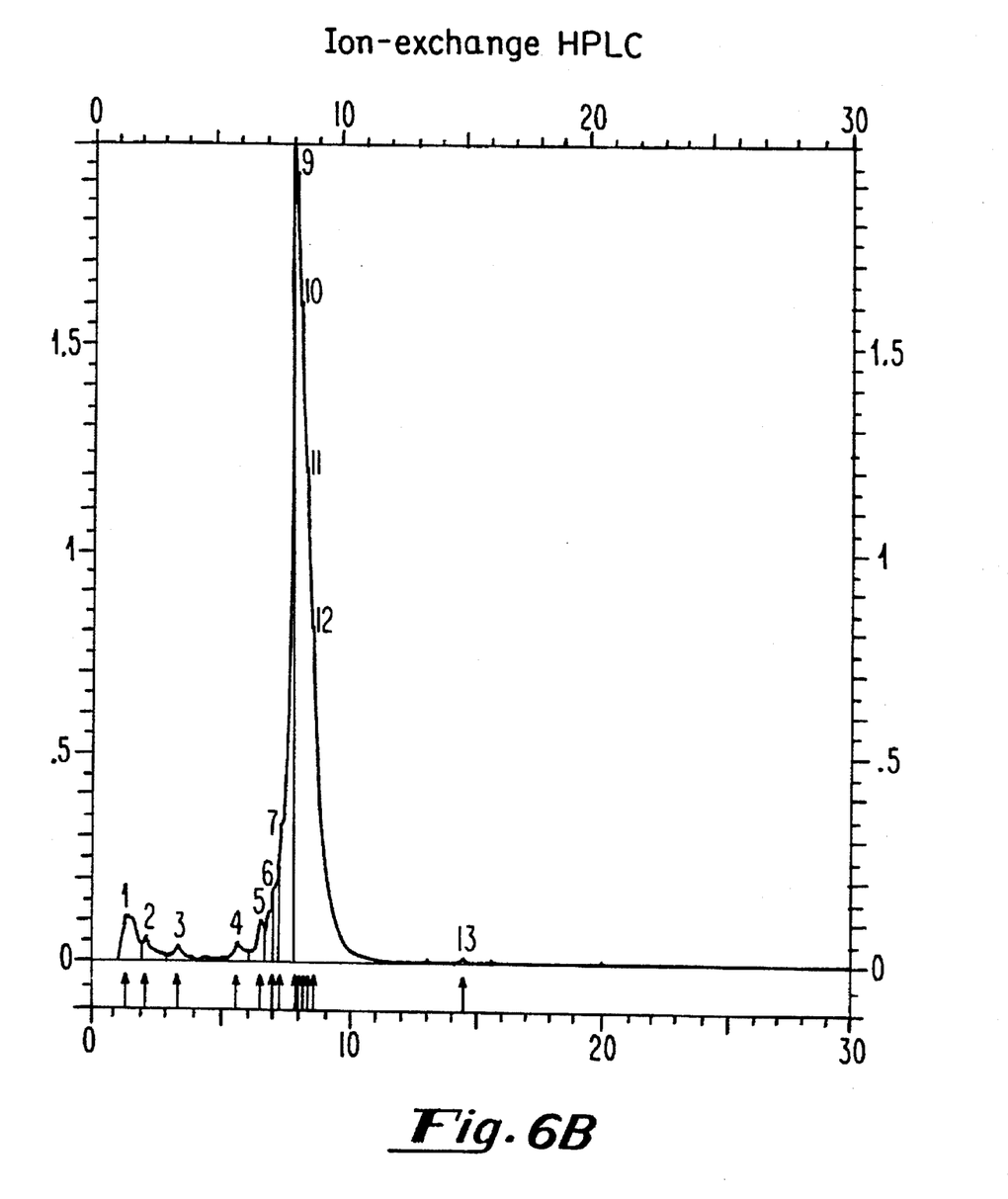
FIG. 6B is a representation of an ionic exchange HPLC trace for a desulfurized oligonucleotide phosphorothioate of the same sequence as is represented in FIG. 4 illustrating a first process condition.
Figure 6C:
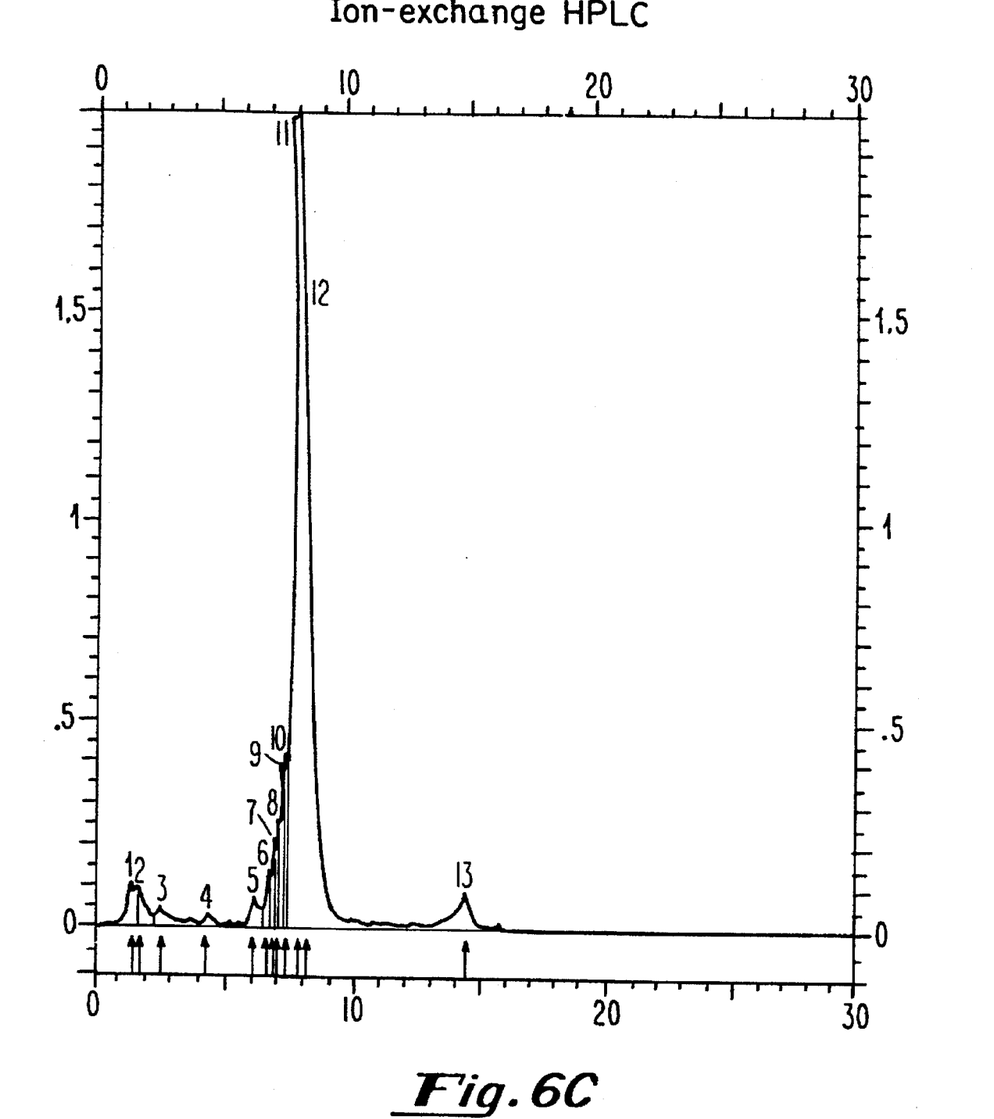
FIG. 6C is a representation of an ionic exchange HPLC trace for a desulfurized oligonucleotide phosphorothioate of the same sequence as is represented in FIG. 4 illustrating a further process condition.
Figure 6D:
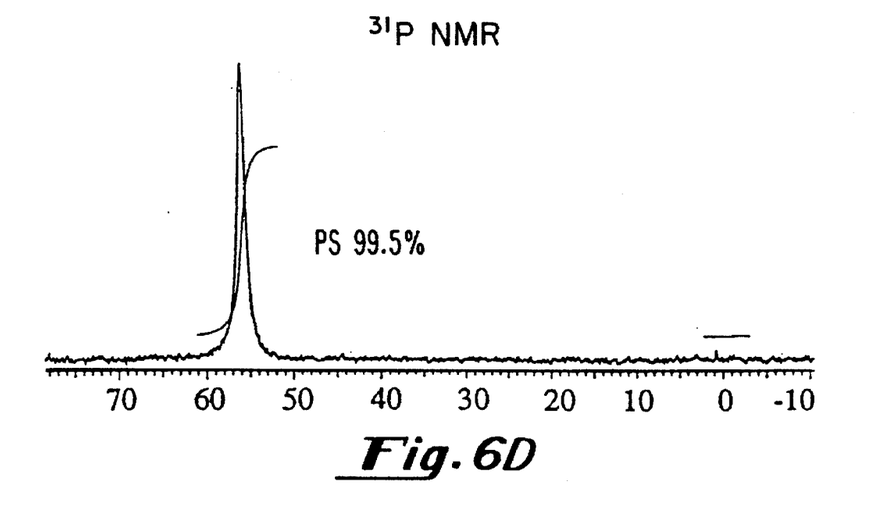
FIG. 6D is a representation of a $^{31}$P NMR trace for a desulfurized oligonucleotide phosphorothioate of the same sequence as is represented in FIG. 4 illustrating starting material.
Figure 6E:
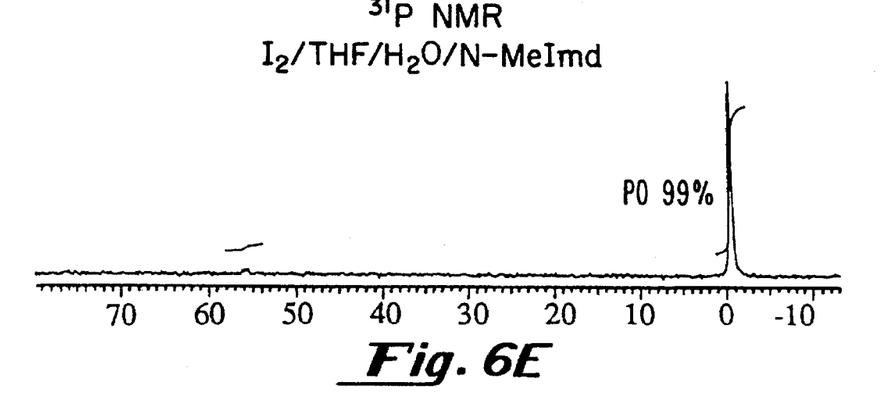
FIG. 6E is a representation of a $^{31}$P NMR trace for a desulfurized oligonucleotide phosphorothioate of the same sequence as is represented in FIG. 4 illustrating a first process condition.
Figure 6F:
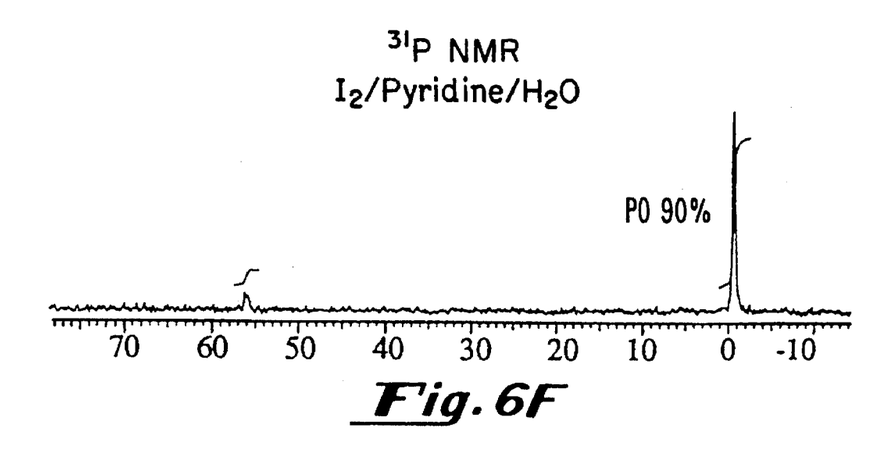
FIG. 6F is a representation of a $^{31}$P NMR trace for a desulfurized oligonucleotide phosphorothioate of the same sequence as is represented in FIG. 4 illustrating a further process condition.

Automatic desulfurization of the oligonucleotides was carried out on ABI synthesizer 394B with application of the cycle 1 (FIGS. 5A–5C). Solid support bearing fully protected oligonucleotide phosphorothioate (0.5 μmoles) was placed in a disposable column used for DNA synthesis and subjected to the cycle 1 (FIGS. 5A–5C). Due to the instability of the desulfurization mixture, solutions containing iodine and N-methyl imidazole need to be prepared as two solutions: A (containing 0.48M solution of iodine in mixture of THF/water, 16/6, v/v) and B (containing mixture of THF/water/N-methylimidazole (16/6/1, v/v/v)), and were mixed during delivery to the column.

The average conversion yield obtained by automatic procedure (99.6–99.8% based on $^{31}$P NMR) suggested that automatic desulfurization is slightly more efficient compared to the manual procedure. The desulfurization procedure did not cause significant degradation of the oligonucleotides even after 24 hours. Chain cleavage products (4.0–4.2 ppm) were monitored by UV and $^{31}$P NMR (UV is more convenient). Degradation was not higher than 0.6–1.5% (based on integration), and recovery of the products from the solid support was comparable with recovery of the starting material.

C. Sequencing

Desulfurized products were cleaved from the support, deprotected in concentrated ammonia according to standard procedure (24 hrs, 55° C.) and analyzed by PAGE, ion-exchange HPLC, and $^{31}$P NMR (FIGS. 2, 4, and 6A–F). Migration of the desulfurized oligonucleotides on PAGE gels was faster, compared to the phosphorothioates. Partially desulfurized oligomers gave characteristic broad peaks on the PAGE gels. These results were consistent with HPLC (FIG. 6) profiles.

Desulfurized and deprotected oligonucleotide products were purified before sequencing using polyacrylamide gel electrophoresis (PAGE).

EXAMPLE 3

Sequencing on the Ion-Exchange Paper

"Desulfurized" oligonucleotides of the sequences TTG CTT CCA TCT TCC TCG TC and GCG TTT GCT CTT CTT CTT GCG were sequenced according to the modified manufacturer's procedure, on the commercially available ion-exchange paper (Hybond M&G from Amersham).

A. Labeling and Purification

Desulfurized and deprotected oligomers were evaporated to dryness on a Speed-Vac, redissolved in an aqueous solution of sodium acetate (300 ml) and precipitated from ethanol (900 ml). This step was repeated twice. Obtained DNA pellet was redissolved in water and 0.5 O.D. of the crude oligonucleotide was transferred to kination buffer and labeled with [γ-$^{32}$P] (60 μmCi) using 2 units of T4 polynucleotide kinase (TPK). Labeled fragments were purified by PAGE (20% gel without urea) and redissolved in water to obtain activity in the range of $5\times10^6$ cpm/100 μl.

B. Immobilization

Labeled oligonucleotides were evaporated to dryness reconstituted in water (to obtain activity $30\times10^5$ cpm/1 μl, heated at 90° C. for 3 minutes and immobilized on the ion-exchange carrier according to the manufacturer's procedure.

C. Modification and Cleavage

Modification reaction of the bases was performed according to the manufacturer's procedure. Reagents used for modification were removed from the support by washing with water. However, it was found that more selective cleavage patterns were obtained for fresh solution used in modification reactions. Paper strips containing modified samples were cut and placed into a set of marked tubes. Cleavage of the modified fragments and removal from the support were performed by heating the paper squares with an aqueous solution of piperidine (10%) for 30 minutes. Then the paper squares were removed from the tubes and samples were frozen and lyophilized under vacuum. Obtained fragments were redissolved in water and evaporated to dryness (three times). It is very important to remove piperidine completely otherwise analysis of the sequence may be difficult.

EXAMPLE 4

Sequence Analysis

Obtained samples were dissolved in loading buffer $30-10^6$ cpm/1 μl and loaded on sequencing gel (25% PAGE, 8M urea) and run at 60 W. After appropriate distance between fragments were obtained gel was dried and sequence patterns were visualized using phosphoroimager (Molecular-Biodynamics).

EXAMPLE 5

Sequencing on Solid Support

A commercially available support developed by Rosental, et al., Nucleic Acids Res., 1985, 13, 1173–1184, was used due to its chemical stability, mechanical resistance, and relatively high loading capacity (up to 200 μg of DNA per $cm^2$). Oligonucleotides desulfurized on the solid support (0.5 O.D. of crude material, having purity in the range of 70% and phosphodiester content 0.6%; purity calculation were based on data obtained from integration of HPLC profiles of crude reaction mixtures. HPLC analysis was performed using ion-exchange column Gem-Pak and gradient 0–60% B/60 min. Buffers: A—86 mM Tris pH=6, B—86 mM Tris pH=6, 2M NaBr, 40% $CH_3CN$ (v/v)) were labeled with [γ-$^{32}$P] ATP, purified using PAGE and immobilized on an ion-exchange carrier. Modification of the bases was performed with: hydroxylamine hydrochloride (pH 6) for C lane, formic acid (88%) for A/G lane, and dimethyl sulfate in ammonium formate buffer (pH 3.5) for G lane. Modification for T/C lane was obtained by treating with 0.2% potassium permanganate (the standard reagent for T/C modification—hydrazine can not be used in combination with the ion-exchange carrier due to removal of the modified fragments from the paper). Oligonucleotide fragments generated by sequencing procedure were fractionated by polyacrylamide gel electrophoresis (PAGE) and visualized using phosphorimager. Phosphorimager analysis was performed using instrument from Molecular Dynamics).

Figure 3A:
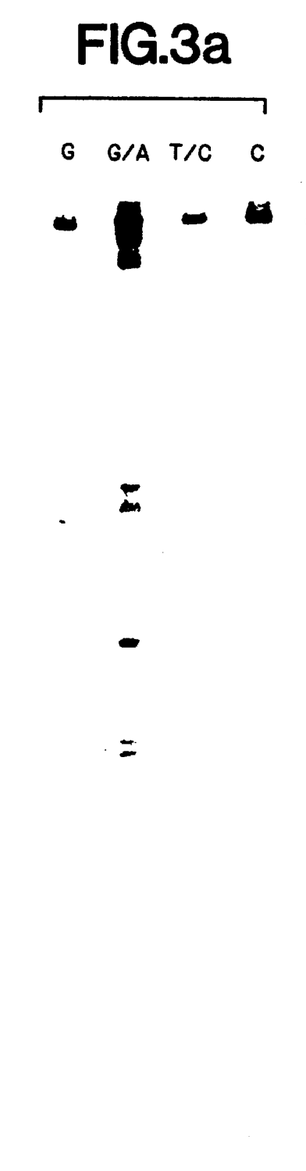
FIG. 3A is a representation of a sequencing gel illustrating direct sequencing of an oligonucleotide phosphorothioate having the sequence GCG TTT GCT CTT CTT CTT GCG.
Figure 3B:
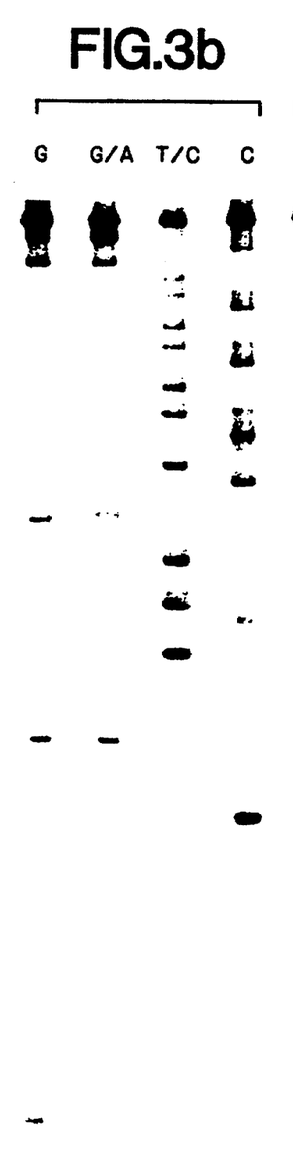
FIG. 3B is a representation of a sequencing gel illustrating the desulfurized phosphorothioate of same oligonucleotide.
Figure 3C:
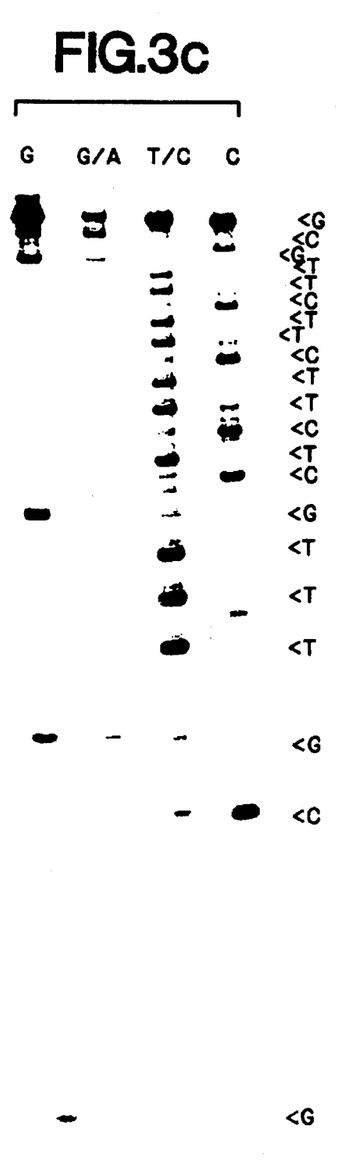
FIG. 3C is a representation of a sequencing gel illustrating the phosphodiester of analogue of the same sequence.
Figure 4:
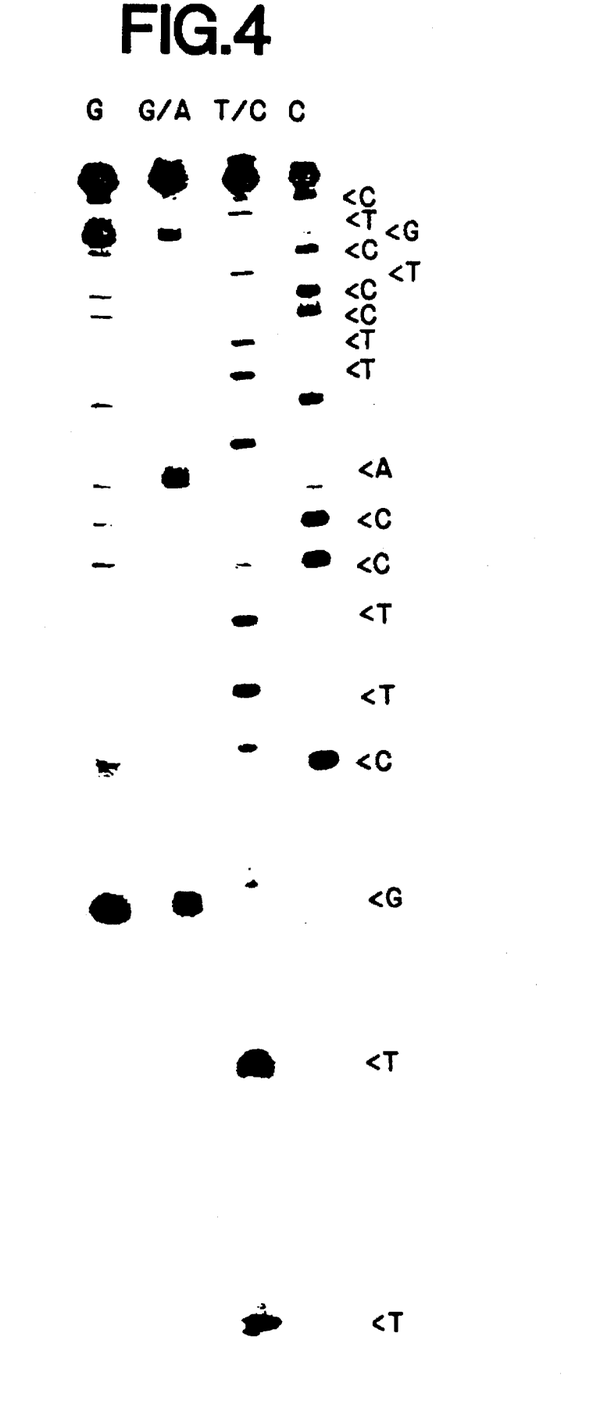
FIG. 4 shows a sequencing gel similar to FIG. 3B for a desulfurized oligonucleotide phosphorothioate of the sequence TTG CTT CCA TCT TCC TCG TC.

We have found that simultaneous sequencing of the desulfurized oligonucleotides and their phosphodiester analogues always generated similar cleavage patterns (FIGS.

3b) and 3c)). Obtained cleavage patterns were clear and the sequence could be easily read. Interestingly enough cleavage patterns of desulfurized oligomers (FIG. 3b)) were more selective, compared to their diesters analogues (FIG. 3c)). It is believed that this phenomenon is related to the incomplete desulfurization. According to the statistical calculation made using binomial equation $(x+y)^n = x^n + nx^{n-1}y + n(n-1)/2! \, x^{n-2}y^2$ where x=fraction of PO and y=fraction of PS and n=20 (for 20-"mer"), oligonucleotide containing 0.6% of phosphorothioate linkages, full length product should has 88.62% of the molecules containing only phosphorodiester linkages, 10.76% molecules containing one phosphorothioate linkage and 0.62% molecules containing two phosphorothioate linkages. Random distribution of phosphorothioate linkages conceivably may lead to less efficient cleavage reactions, causing "fine tuning" effect during the cleavage of the modified fragments.

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 21
        ( B ) TYPE: nucleotide
        ( C ) STRANDEDNESS: single
        ( D ) TOPOLOGY: unknown     ( i i ) SEQUENCE DESCRIPTION: SEQ ID NO: 1:

GCG TTT GCT CTT CTT CTT GCG                             2 1

( 2 ) INFORMATION FOR SEQ ID NO: 2:

( i ) SEQUENCE CHARACTERISTICS:
        ( A ) LENGTH: 20
        ( B ) TYPE: nucleotide
        ( C ) STRANDEDNESS: single
        ( D ) TOPOLOGY: unknown     ( i i ) SEQUENCE DESCRIPTION: SEQ ID NO: 2:

TTG CTT CCA TCT TCC TCG TC                               2 0

What is claimed is:

1. A method for desulfurizing a phosphate protected phosphorothioate oligonucleotide synthesized on a solid phase support comprising the steps of:
  a) removing the phosphate protecting groups before removal of said oligonucleotide from said solid phase support; and
  b) treating said deprotected oligonucleotide with an iodine solution comprising at least about 15 equivalents of iodine per sulfur atom of the oligonucleotide.

2. The method of claim 1 wherein said iodine is in a solution comprising tetrahydrofuran, water, and N-methylimidazole.

3. The method of claim 2 wherein said tetrahydrofuran, water, and N-methylimidazole are present in a volume ratio of about 16/6/1.

4. The method of claim 1 wherein said phosphate protecting group is a cyanoethyl protecting group.

5. The method of claim 1 wherein said oligonucleotide comprises from 10 to about 50 nucleotide units.

6. The method of claim 4 wherein said removal of the protecting groups comprises treatment with t-butylamine in pyridine.

7. The method of claim 1 wherein said treating b) step is continued for a period of time sufficient to remove at least about 98% of the sulfur from the oligonucleotide.

8. The method of claim 1 wherein the iodine is present in an amount of at least about 20 equivalents for every equivalent of sulfur.

9. A method for desulfurizing a cyanoethyl protected phosphorothioate oligonucleotide bound to a solid support comprising treating the bound oligonucleotide with an iodine solution for a period of time effective to desulfurize said oligonucleotide.

10. The method of claim 9 wherein said iodine solution is prepared by premixing first and second independent solutions during delivery to the solid support, the first solution comprising iodine and tetrahydrofuran/water, the second solution comprising tetrahydrofuran/water/N-methylimidazole.

11. The method of claim 10 wherein the first solution comprises tetrahydrofuran and water in a volume ratio of about 16/6.

12. The method of claim 10 wherein the second solution is tetrahyrofuran, water, and N-methylimidazole in a volume ratio of about 16/6/1.

13. The method of claim 10 wherein the concentration of iodine in said solution is between about 0.40M to 0.55M.

14. The method of claim 9 further comprising the steps of:
  a) labeling the desulfurized oligonucleotide;
  b) purifying the labeled oligonucleotide product of step a);
  c) immobilizing said purified oligonucleotide of step b) on an ion-exchange carrier;
  d) modifying the base units of said oligonucleotide from step c), thereby generating oligonucleotide fragments forming lanes of guanine, adenine and guanine, thymine and cytosine;

e) fractioning said oligonucleotide fragments; and f) imaging said oligonucleotide fragments.

15. The method of claim 14 wherein said oligonucleotide is labeled with ATP and polynucleotide kinase.

16. The method of claim 14 wherein said oligonucleotide is purified using polyacrylamide gel electrophoresis.

17. The method of claim 14 wherein step d) further comprises treating the cytosine lane with hydroxylamine hydrochloride at about pH 6.

18. The method of claim 14 wherein step d) further comprises treating the adenine/guanine lane with solution of formic acid.

19. The method of claim 14 wherein step d) further comprises treating the guanine lane with ammonium formate buffer having a pH of about 3.5.

20. The method of claim 14 wherein step d) further comprises treating the thymine/cytosine lane with a potassium permanganate solution.

21. The method of claim 14 wherein said imaging is performed using a phosphoroimager.

22. The method of claim 14 wherein said ion-exchange carrier comprises cellulose.

23. The method of claim 9 wherein said oligonucleotide contains from 10 to about 50 nucleotide units.

24. A method for desulfurizing a phosphate protected phosphorothioate oligonucleotide synthesized on a solid phase support comprising the steps of:

a) removing the phosphate protecting groups before removal of said oligonucleotide from said solid phase support; and b) treating said deprotected oligonucleotide with an iodine solution comprising at least about 10 equivalents of iodine per sulfur atom of the oligonucleotide.

* * * * *